United States Patent
Aoki

(10) Patent No.: US 7,476,446 B2
(45) Date of Patent: Jan. 13, 2009

(54) SILICONE ADHESIVE COMPOSITION AND AN ADHESIVE TAPE THEREOF

(75) Inventor: Shunji Aoki, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/896,244

(22) Filed: Aug. 30, 2007

(65) Prior Publication Data

US 2008/0003439 A1 Jan. 3, 2008

Related U.S. Application Data

(60) Division of application No. 11/410,926, filed on Apr. 26, 2006, now Pat. No. 7,329,464, which is a continuation-in-part of application No. 10/721,276, filed on Nov. 26, 2003, now abandoned.

(30) Foreign Application Priority Data

Nov. 28, 2002 (JP) ............................. 2002-344919

(51) Int. Cl.
*B32B 25/20* (2006.01)

(52) U.S. Cl. ..................... 428/447; 524/588; 524/96; 528/31; 528/32

(58) Field of Classification Search ................ 428/447; 524/588, 96; 528/31, 32
See application file for complete search history.

(56) References Cited

U.S. PATENT DOCUMENTS

| 3,509,241 | A | 4/1970 | De Paolo et al. |
| 5,248,739 | A | 9/1993 | Schmidt et al. |
| 6,730,397 | B2 | 5/2004 | Melancon et al. |
| 2003/0082388 | A1 | 5/2003 | Carter et al. |

FOREIGN PATENT DOCUMENTS

| JP | 2001-345415 A1 | 12/2001 |
| JP | 2003-096429 A1 | 4/2003 |

*Primary Examiner*—Kuo-Liang Peng
(74) *Attorney, Agent, or Firm*—Birch, Stewart, Kolasch & Birch, LLP

(57) ABSTRACT

A peroxide curable silicon adhesive composition comprising a diorganopolysiloxane (A), a polyorganosiloxane (B) comprising $R^1{}_3SiO_{0.5}$ unit and $SiO_2$ unit in a molar ratio of the $R^1{}_3SiO_{0.5}$ unit to the $SiO_2$ unit of from 0.6 to 1.7, a hindered amine compound (C), and an organic peroxide (D), and an adhesive tape thereof are provided. Also provided are an addition-reactive silicon adhesive composition comprising a diorganopolysiloxane (A') having 2 or more alkenyl groups, a polyorganosiloxane (B), a hindered amine compound (C), a polyorganosiloxane (E) having SiH group, a retarder (F), and a platinum catalyst (G), and an adhesive tape thereof.

6 Claims, No Drawings

SILICONE ADHESIVE COMPOSITION AND AN ADHESIVE TAPE THEREOF

CROSS REFERENCE

This application is a Divisional of application Ser. No. 11/410,926, filed on Apr. 26, 2006, now U.S. Pat. No. 7,329,464 which is a Continuation-In-Part of application Ser. No. 10/721,276 filed on Nov. 26, 2003, now abandoned, the entire contents of which is incorporated by reference for which priority is claimed under 35 U.S.C. §120.

FIELD OF THE INVENTION

This invention relates to a silicone pressure sensitive adhesive composition and a pressure sensitive adhesive tape thereof which does not leave adhesive residue when the tape which is applied on a substrate such as stainless steel and heat-aged at 280 degrees C. is peeled off.

DESCRIPTION OF THE PRIOR ART

Adhesive tapes and labels with silicone adhesive are excellent in heat resistance, cold resistance, weather resistance, electrical insulation, and chemical resistance and, therefore, used in severe environments where acrylic adhesives, rubber adhesives, urethane adhesives, or epoxy adhesives are damaged and degraded.

In manufacturing or processing mechanical parts, masking or temporary fixing of the parts are occasionally required. For these purposes, a silicone adhesive tape is suited which can be peeled off even after heated at 250 degrees C. However, heating at a higher temperature is practiced recently, and an improvement in the heat resistance is required.

For example, in a solder reflow process to solder electronic parts to boards, a reflow temperature is higher than ever and a peak temperature sometimes reach 280 degrees C., as lead-free solder became practical. Even at such a high temperature, an adhesive should not come off and, after the reflow process, should be peeled off without leaving any adhesive residue on an object to which the adhesive was applied.

When some adhesive tapes with conventional silicone adhesive are applied on metal to mask the metal and, then, exposed to a temperature of from 150 to 250 degrees C., and peeled off, the adhesive or an adhesive layer transfers from a base film of the adhesive tape to the metal. This transferred adhesive is referred to as adhesive residue. This is caused in the following mechanism. The silicone adhesive is degraded by heat oxidation; this weakens cohesive strength of the adhesive layer; and the adhesive layer is broken when peeled off.

Meanwhile, Japanese Patent Application Laid-open No.2001-345415 discloses an adhesive tape where an antioxidant is incorporated in a silicone adhesive. Then, the adhesive does not degrade even when heated to about 200 degrees C. for some hours in production processes of semiconductor devices or electronic parts provided with copper lead frames.

Japanese Patent Application No.2001-290863 by the present applicant discloses a silicone adhesive tape comprising a phenolic antioxidant. The tape does not leave the adhesive residue even when heated to about 150 to 250 degrees C.

However, when the above tape containing the antioxidant is exposed to heating to 280 degrees C. or higher, especially when applied on metals such as copper, copper alloys or iron, the adhesive residue is left on the metals when the tape is peeled off.

Thus, an object of the present invention is to provide a silicone adhesive composition and an adhesive tape thereof which can be peeled off without leaving adhesive residue when applied on an object made of metal, particularly stainless steel, to mask them and heated to a temperature so high as 280 degrees C.

SUMMARY OF THE INVENTION

The present inventor has found that, by adding a particular hindered amine compound to a silicone adhesive composition, the adhesive can be peeled off without leaving adhesive residue when applied on metals, particularly stainless steel, heat aged at 280 degrees C., and peeled off after.

Thus, the present invention is a peroxide curable silicon adhesive composition comprising 20 to 80 parts by weight of a diorganopolysiloxane (A), 80 to 20 parts by weight of a polyorganosiloxane (B) comprising $R^1{}_3SiO_{0.5}$ unit and $SiO_2$ unit in a molar ratio of the $R^1{}_3SiO_{0.5}$ unit to the $SiO_2$ unit of from 0.6 to 1.0, wherein $R^1$ is a monovalent hydrocarbon group having 1 to 10 carbon atoms, 0.01 to 1.0 part by weight, based on a total of (A) and (B) of 100 parts by weight, of a hindered amine compound (C) having the moiety represented by the following formula,

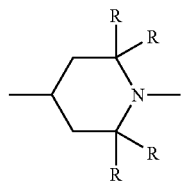

wherein R is a monovalent hydrocarbon group having 1 to 6 carbon atoms, and 0.1 to 5.0 parts by weight, based on a total of (A) and (B) of 100 parts by weight, of an organic peroxide (D).

Also, the present invention is an addition-reactive silicon adhesive composition comprising 20 to 80 parts by weight of a diorganopolysiloxane (A') having 2 or more alkenyl groups, 80 to 20 parts by weight of a polyorganosiloxane (B) comprising $R^1{}_3SiO_{0.5}$ unit and $SiO_2$ unit in a molar ratio of the $R^1{}_3SiO_{0.5}$ unit to the $SiO_2$ unit of from 0.6 to 1.0, wherein $R^1$ is a monovalent hydrocarbon group having 1 to 10 carbon atoms, 0.01 to 1.0 part by weight, based on a total of (A') and (B) of 100 parts by weight, of a hindered amine compound (C) having the moiety represented by the following formula,

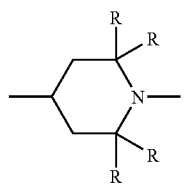

wherein R is a monovalent hydrocarbon group having 1 to 6 carbon atoms, a polyorganosiloxane (E) having SiH group in such an amount that a molar ratio of the SiH group to the alkenyl group of the component (A') ranges from 0.5 to 20, 0 to 8.0 part by weight, based on a total of (A') and (B) of 100 parts by weight, of a retarder (F), and a platinum catalyst (G) in such an amount that an amount as platinum ranges from 1 to 5000 ppm based on a total of (A') and (B) of 100 parts by weight.

The present invention also provides an adhesive tape comprising a plastic film and an adhesive applied on at least one side of the plastic film, the adhesive being made by curing any one of the adhesive compositions above.

The silicone adhesive tape above is useful as a masking tape for metals, particularly stainless steel.

DESCRIPTION OF THE PREFERRED EMBODIMENTS

Component (A) is a diorganopolysiloxane, preferably, represented by any one of the following formulae:

$$R^2{}_3SiO-(R^2{}_2SiO)_p-SiR^2{}_3$$

$$R^2{}_2(HO)SiO-(R^2{}_2SiO)_p-SiR^2{}_2(OH)$$

wherein $R^2$ may be the same with or different from each other and is a hydrocarbon group having 1 to 10 carbon atoms. To improve heat resistance, $R^2$ is selected so that 0 to 35 mole %, particularly from 2 to 20 mole %, of the whole organic groups bonded to the silicon atoms is a phenyl group. In addition, 1 to 35 mole %, particularly 2 to 20 mole %, of the whole siloxane unit is preferably a diphenylsiloxane unit. In the formulae, p is such a number that a viscosity at 25 degrees C. of component (A) is 500 mPa·s or higher.

Preferably, $R^2$ is a monovalent hydrocarbon group having 1 to 10 carbon atoms such as an alkyl group, e.g., methyl, ethyl, propyl, and butyl group; an alicyclic group, e.g., cyclohexyl group; and an aryl group, e.g., phenyl and tolyl group, among which methyl and phenyl groups are preferred.

The diorganopolysiloxane (A) may preferably be oily or gummy. Oily component (A) preferably has a viscosity at 25 degrees C. of 500 mPa·s or higher, particularly 10,000 mPa·s or higher. If the viscosity is below the aforesaid lower limit, a composition may not be cured enough, or cohesive strength, i.e., holding power, may be undesirably smaller. When component (A) is gummy, a viscosity of a 30 wt % solution of it in toluene is preferably 100,000 mPa·s or lower. If the viscosity exceeds the aforesaid upper limit, a composition may be so viscous that the composition is difficult to be agitated in its preparation process. The component (A) may be a mixture of two or more kinds of the diorganopolysiloxane.

Component (B) is a polyorganosiloxane comprising $R^1{}_3SiO_{0.5}$ unit and $SiO_2$ unit in a molar ratio of $R^1{}_3SiO_{0.5}$ unit to $SiO_2$ unit of from 0.6 to 1.0, preferably from 0.7 to 0.9. If the ratio is below the aforesaid lower limit, adhesion strength or tack may be lower. If the ratio exceeds the aforesaid upper limit, adhesion strength or holding power maybe lower. $R^1$ is a monovalent hydrocarbon group having 1 to 10 carbon atoms such as an alkyl group, e.g., methyl, ethyl, propyl, and butyl group, an alicyclic group, phenyl group, vinyl group, allyl group and hexenyl group, among which a methyl group is preferred.

Component (B) preferably has a number average molecular weight, determined by GPC using polystyrene standards, of from 1,700 to 5,000, preferably from 1,800 to 4,000. An adhesive composition comprising a polyorganosiloxane with a number average molecular weight below the aforesaid lower limit may show low adhesive strength, holding power, or high adhesive residue. A composition comprising a polyorganosiloxane with a number average molecular weight below the aforesaid lower limit may also show low adhesive strength and tack or tackiness.

Component (B) may have an OH-group in an amount of 4.0 wt % or smaller based on a total weight of component (B). If the amount exceeds the upper limit, a curing property of the adhesive composition may be poorer. Component (B) may also have $R^1SiO_{0.5}$ unit and/or $R^1{}_2SiO$ unit in such amounts that properties of the present composition are not spoiled. Component (B) may be a mixture of two or more kinds of the polyorganosiloxane.

Components (A) and (B) may be simply blended or a condensation product of (A) and (B) may be used when component (A) comprises the following diorganopolysiloxane $$R^2{}_2(HO)SiO-(R_{22}SiO)_p-SiR^2{}_2(OH)$$

wherein p is as previously described. The condensation reaction may be carried out by dissolving a mixture of components (A) and (B) in a solvent such as toluene and subjecting the mixture to a reaction in the presence of an alkaline catalyst at room temperature to a refluxing temperature.

Preferably, a weight ratio of component (A) to (B) ranges from 20/80 to 80/20, particularly from 30/70 to 70/30. If the ratio is below the aforesaid lower limit, adhesion strength and holding power may be smaller. If the ratio exceeds the aforesaid upper limit, adhesion strength and tack may be lower.

Component (C) is a compound having the following hindered amine moiety.

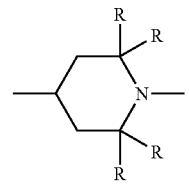

wherein R is a hydrocarbon group having 1 to 6 carbon atoms such as an alkyl group, e.g., methyl, ethyl, propyl, and butyl group; an alicyclic group, e.g., cyclohexyl group; and an aryl group, e.g., phenyl group, among which a methyl group is particularly preferred.

Examples of the preferred component (C) are shown below.

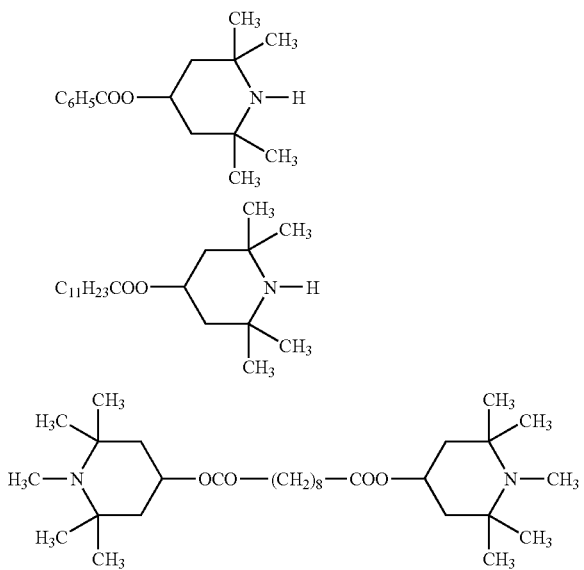

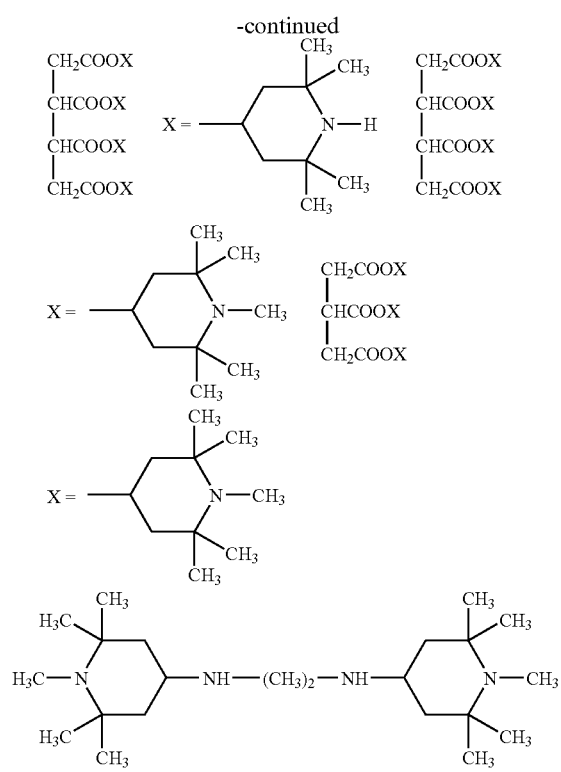
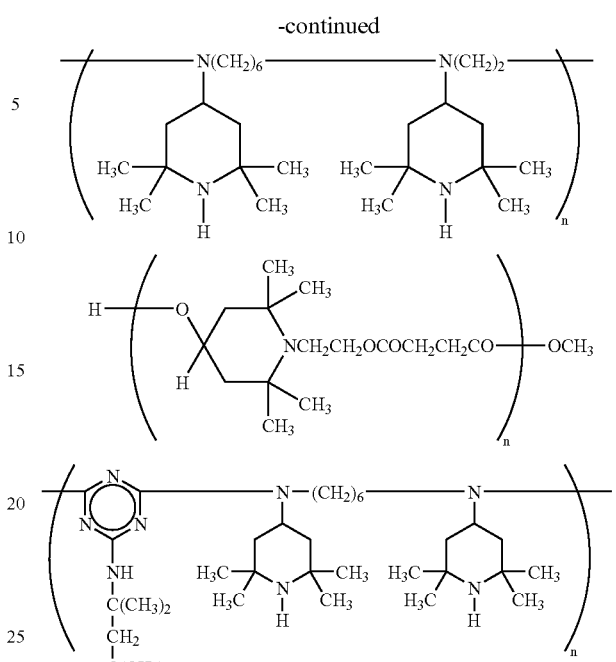
wherein n is an integer of from 2 to 20. Other examples of the component (C) are shown below.
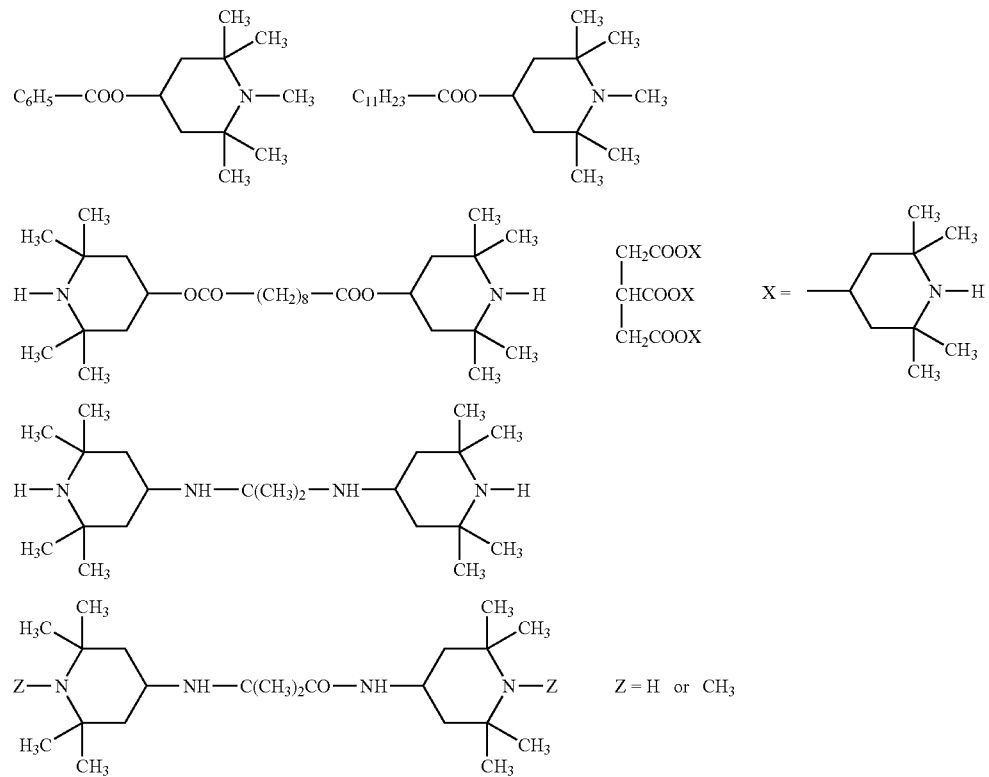

-continued
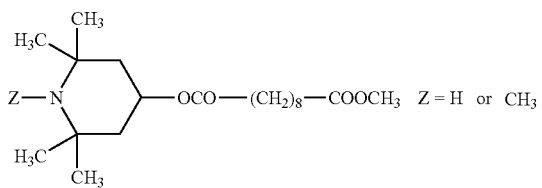
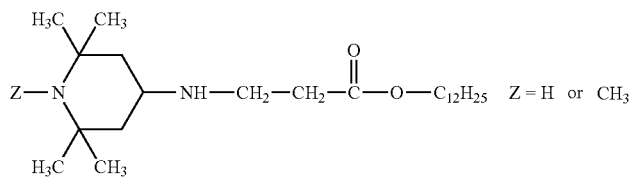
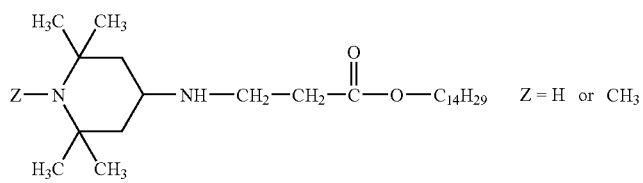
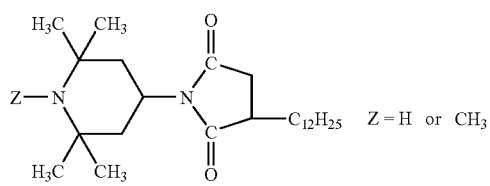
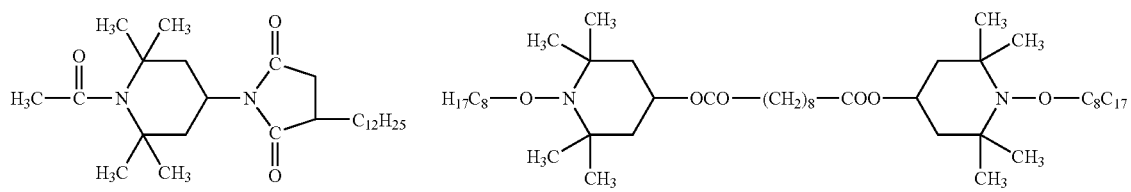
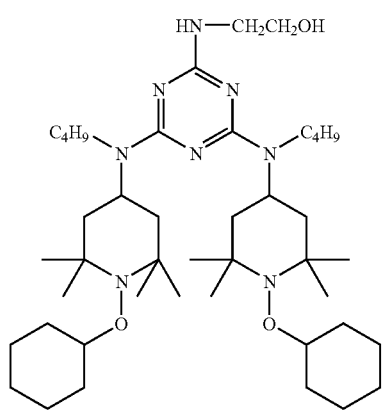

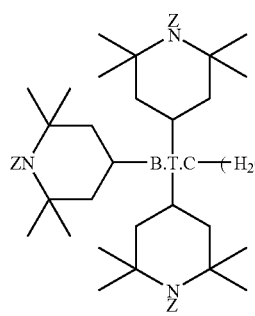 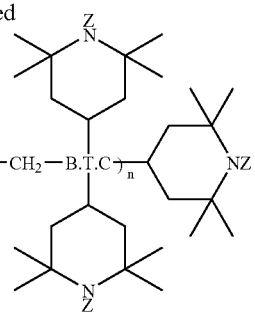
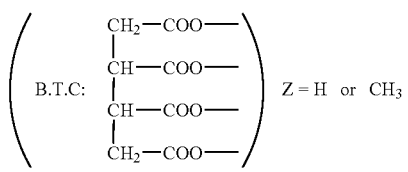
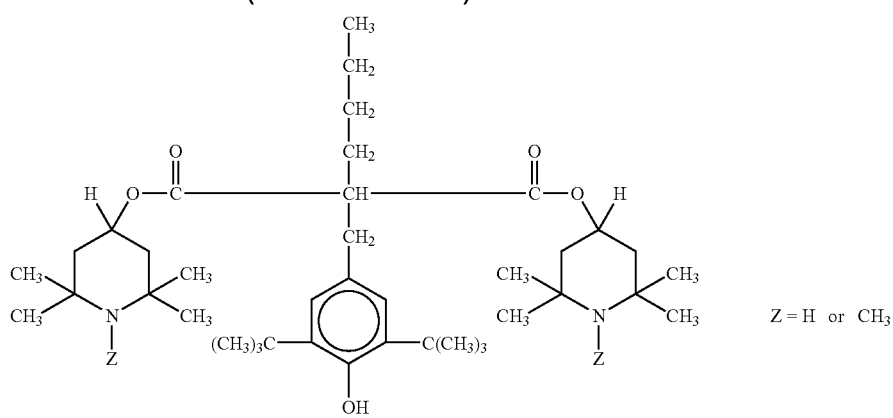
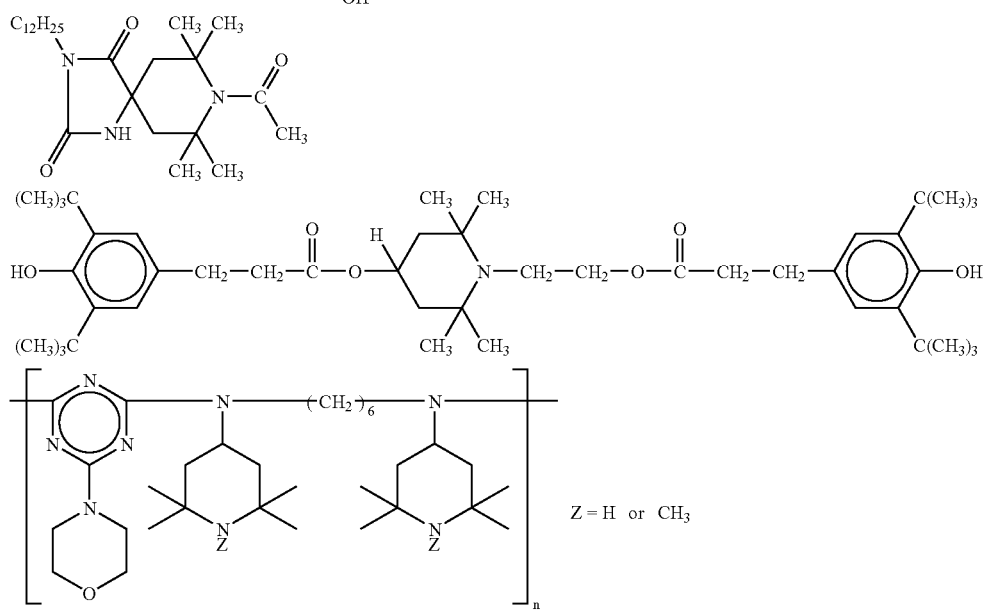
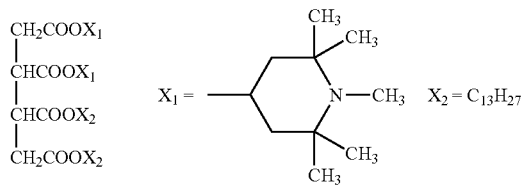 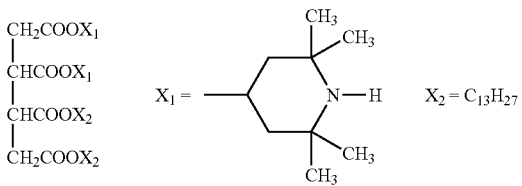

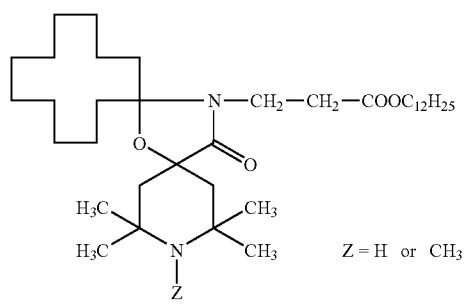
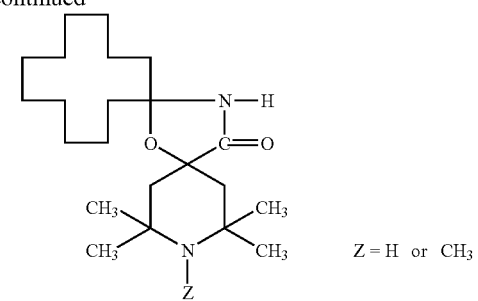
-continued
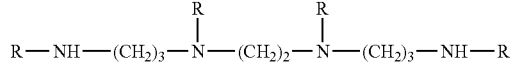
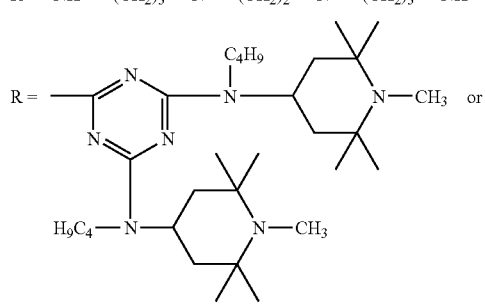
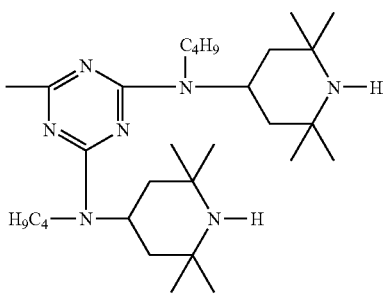
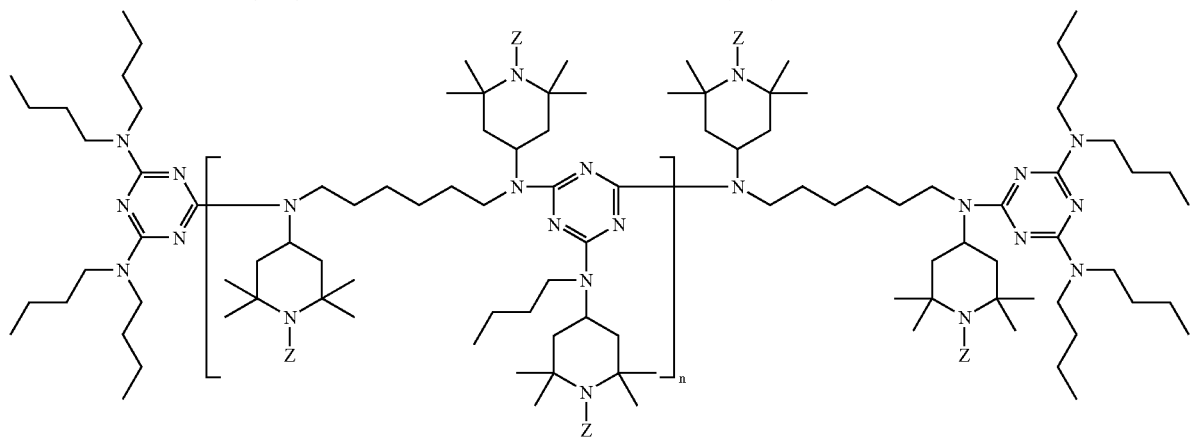
Z = H or CH$_3$
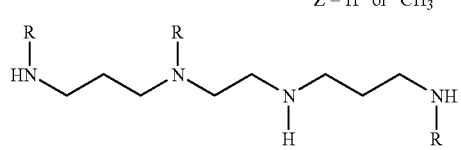
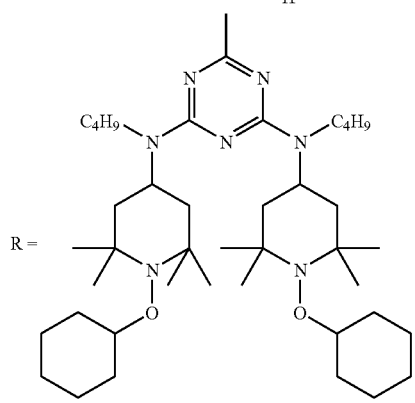

Component (C) is incorporated in an amount, based on a total of components (A) and (B) of 100 parts by weight, of 0.01 to 1 part by weight, preferably 0.05 to 0.5 part by weight. If the amount is below the aforesaid lower limit, heat resistance may not be improved. If the amount exceeds the aforesaid upper limit, holding power may be smaller. Component (C) may be a mixture of two or more kinds of the hindered amine compounds.

Component (D) is an organic peroxide such as dibenzoyl peroxide, 4,4'-dimethylbenzoyl peroxide, 3,3'-dimethyldibenzoyl peroxide, 2,2'-dimethyldibenzoyl peroxide, 2,2', 4,4'-tetrachloro dibenzoyl peroxide, and cumyl peroxide.

Component (D) is incorporated in an amount, based on a total of components (A) and (B) of 100 parts by weight, of from 0.1 to 5 parts by weight, preferably from 1 to 4 parts by weight. If the amount is below the aforesaid lower limit, curing may be poorer and holding power may be lower. If the amount exceeds the aforesaid upper limit, discoloration may occur and holding power may be lower. Component (D) may be used as such or in any form, for example, a solution in an organic solvent, a dispersion in water, and a paste in silicone oil. Component (D) maybe a mixture of two or more kinds of the organic peroxide.

The present addition-reactive silicon adhesive composition comprises 20 to 80 parts by weight of diorganopolysiloxane (A') having 2 or more alkenyl groups, 80 to 20 parts by weight of polyorganosiloxane (B) comprising $R^1_3SiO_{0.5}$ unit and $SiO_2$ unit in a molar ratio of the $R^1_3SiO_{0.5}$ unit to the $SiO_2$ unit of from 0.6 to 1.0, wherein $R^1$ is a monovalent hydrocarbon group having 1 to 10 carbon atoms, 0.01 to 1.0 part by weight, based on a total of (A') and (B) of 100 parts by weight, of a hindered amine compound (C) having the moiety represented by the following formula,

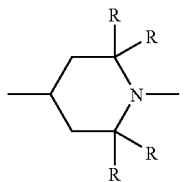

wherein R is a monovalent hydrocarbon group having 1 to 6 carbon atoms, a polyorganosiloxane (E) having SiH group in such an amount that a molar ratio of the SiH group to the alkenyl group of the component (A') ranges from 0.5 to 20, 0 to 8.0 part by weight, based on a total of (A') and (B) of 100 parts by weight, of a retarder (F), and a platinum catalyst (G) in such an amount that an amount as platinum, based on a total of (A') and (B) of 100 parts by weight, ranges from 1 to 5000 ppm. The present invention also provides an adhesive tape comprising a plastic film and an adhesive applied on at least one side of the plastic film, the adhesive being made by curing the silicone adhesive composition above.

The silicone adhesive composition and adhesive tape are useful to mask metals, especially stainless steel.

Component (A') is a polyorganosiloxane having an alkenyl group, preferably represented by either one of the following formulae.

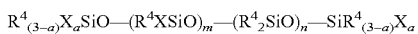

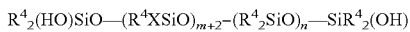

wherein $R^4$ is a monovalent hydrocarbon group free of an aliphatic unsaturated bond; X is an organic group having an alkenyl group; a is an integer of from 0 to 3, preferably 1; m is the number of at least 0; n is the number of at least 100; a and m are not zero at the same time, and m+n is such umber that a viscosity of the diorganopolysiloxane at 25 degrees C. is 500 mPa·s or higher.

Preferably, $R^4$ is a group having 1 to 10 carbon atoms such as an alkyl group, e.g., methyl, ethyl, propyl, and butyl group; an alicyclic group, e.g., cyclohexyl group; and an aryl group, e.g., phenyl and tolyl group, among which methyl and phenyl groups are particularly preferred.

Examples of preferred X having an alkenyl group include those having 2 to 10 carbon atoms such as vinyl, allyl, hexenyl, octenyl, acryloylpropyl, acryloylmethyl, methacryloylpropyl, cyclohexenylethyl, and vinyloxypropyl groups, among which a vinyl group is particularly preferred.

The diorganopolysiloxane (A') may be oily or gummy. When component (A') is oily, it preferably has a viscosity at 25 degrees C. of 1000 mPa·s or higher, particularly 10,000 mPa·s or higher. If the viscosity is below the aforesaid lower limit, a curing property of the composition may not be good or cohesive strength, i.e., holding power, may be undesirably smaller. When component (A') is gummy, it preferably has a viscosity in a 30 wt % solution in toluene of 100,000 mPa·s or lower. If the viscosity exceeds the aforesaid upper limit, a composition may be so viscous that the composition is difficult to be agitated in a preparation process. The component (A') may be a mixture of two or more kinds of the diorganopolysiloxane.

Component (B) is as described above.

Components (A') and (B) may be simply blended or a condensation product of (A') and (B) may be used when component (A) comprises the following diorganopolysiloxane

wherein m, n and $R^4$ are described above. The condensation reaction may be carried out by dissolving a mixture of components (A) and (B) in a solvent such as toluene and subjecting the mixture to a reaction in the presence of an alkaline catalyst at room temperature to a refluxing temperature.

A weight ratio of component (A') to (B) ranges from 20/80 to 80/20, preferably from 30/70 to 70/30. If the ratio is below the aforesaid lower limit, adhesion and/or holding power may be smaller. If the ratio exceeds the aforesaid upper limit, adhesion and/or tack may be smaller.

Component (C) is a hindered amine compound as described above.

Component (E) is an organohydrogenpolysiloxane crosslinking agent having at least 2, preferably at least 3, hydrogen atoms bonded to silicon atoms and may be linear, branched or cyclic. Examples of (E) are as shown below, but not limited thereto.

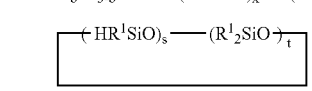

wherein $R^1$ is the hydrocarbon group described above; b is 0 or 1; x and y are such integers that the organohydrogenpolysiloxane has a viscosity of from 1 to 5,000 mPa·s at 25 degrees C.; s is an integer of 2 or larger; t is an integer of 0 or larger; and the sum of s and t is 3 or larger, preferably from 3 to 8.

Preferably, a viscosity at 25 degrees C. of the organohydrogenpolysiloxane ranges from 1 to 5,000 mPa·s, more preferably from 5 to 500 mPa·s. Component (E) may be a mixture of two or more of the organohydrogenpolysiloxane.

Component (E) may be used in such an amount that a molar ratio of the SiH group in component (E) to the alkenyl group of component (A') ranges from 0.5 to 20, preferably from 0.8 to 15. If the ratio is below the aforesaid lower limit, crosslinking density may be lower to give lower holding power. If the ratio exceeds the aforesaid upper limit, crosslinking density may be so high that adhesion strength and tack may not be enough, and, sometimes, a pot life may be shorter.

Component (F) is a retarder which prevents the adhesive composition from becoming thicker or from gelling during the preparation of the composition or before heat curing the composition applied on a substrate. Examples of component (F) include 3-methyl-1-butyn-3-ol, 3-methyl-1-pentyn-3-ol, 3,5-dimethyl-1-hexyn-3-ol, 1-etynylcyclohexanol, 3-methyl-3-trimethylsiloxy-1-butyn, 3-methyl-3-trimethylsiloxy-1-pentyn, 3,5-dimethyl-3-trimethylsiloxy-1-hexyn, 1-ethynyl-1-trimethysiloxy cyclohexane, bis(2,2-dimethyl-3-butynoxy)dimethyl silane, 1,3,5,7-tetramethyl-1,3,5,7-tetravinyl cyclotetrasiloxane, and 1,1,3,3-tetramethyl-1,3-divinyl disiloxane.

Preferably, component (F) is incorporated in the composition in an amount, based on a total of components (A') and (B) of 100 parts by weight, of from 0 to 8.0 parts by weight, more preferably 0.05 to 2.0 parts by weight. If the amount exceeds the aforesaid upper limit, the composition may not be cured enough.

Component (G) is a platinum catalyst such as chloroplatinic acid, alcohol solutions of chloroplatinic acid, reaction products of chloroplatinic acid with alcohols, reaction products of chloroplatinic acid with olefin compounds, and reaction products of chloroplatinic acid with siloxane having a vinyl group.

Component (G) is incorporated in the composition preferably in such an amount that the amount as platinum ranges from 1 to 5,000 ppm, particularly from 5 to 2,000 ppm. If the amount is below the aforesaid lower limit, insufficient curing, lower crosslinking density and smaller holding power may occur. If the amount exceeds the aforesaid upper limit, a serviceable time of the composition may be shorter.

To the addition-reactive silicone adhesive composition, a phenolic antioxidant, referred to as component (H) hereinafter, may be added. Preferably, component (H) has the following structure.

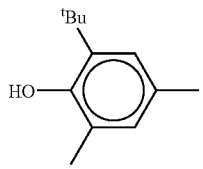

Examples of component (H) are as shown below.

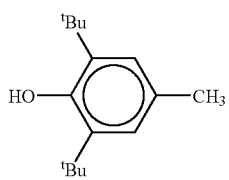

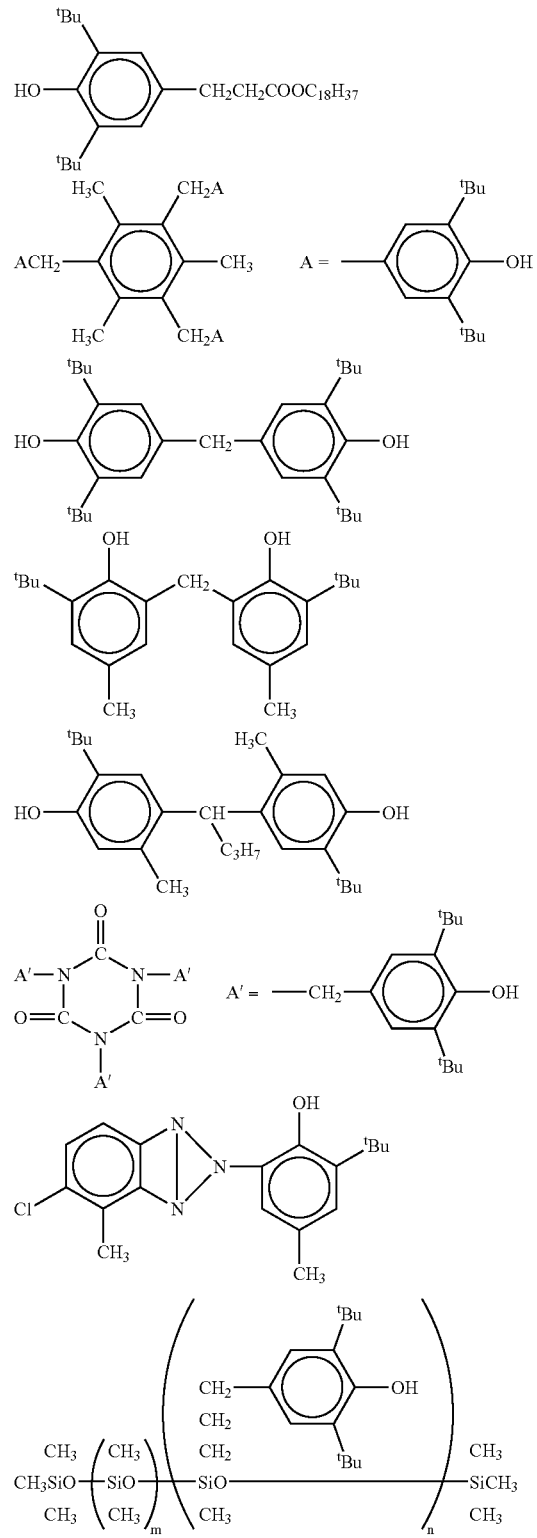

wherein m is 0 or larger, and n is an integer of at least 1.

Component (H) may be incorporated in the composition in an amount, based on a total of components (A') and (B) of 100 parts by weight, of from 0.1 to 10 parts by weight. If the amount is below the aforesaid lower limit, the adhesive residue may not be sufficiently prevented after the composition is exposed to a high temperature. If the amount exceeds the aforesaid upper limit, holding power may be lower.

In addition to the above components, the present silicone adhesive composition may comprise optional components. Examples of such components include non-reactive polyorganosiloxanes such as polydimethylsiloxane and polydimethyldiphenylsiloxane; antioxidants such as phenol type, quinone type, amine type, phosphorus type, phosphite type, sulfur type, and thioether type antioxidants; photostabilizers such as triazole type and benzophenone type photostabilizers; flame retardants such as phosphate ester type, halogen type, phosphorus type, and antimony type flame retardants; antistatic agents such as cationic surfactants, anionic surfactants, and nonionic surfactants; solvents for lowering the viscosity in application, for example, aromatic solvents such as toluene and xylene, aliphatic solvents such as hexane, octane and isoparaffins, ketones such as methyl ethyl ketone and methyl isobutyl ketone, esters such as ethyl acetate and isobutyl acetate, and ethers such as diisopropyl ether and 1,4-dioxane; and mixtures thereof; and dyes and pigments.

The silicone adhesive composition as described above may be applied on various kinds of substrates and cured in predetermined conditions to form an adhesive layer. Examples of the substrates include plastic films such as films of polyester, polytetrafluoroethylene, polyimide, polyphenylene sulfide, polyamide, polycarbonate, polystyrene, polypropylene, polyethylene, and polyvinyl chloride; metal foils such as aluminum foil and copper foil; papers such as Japanese paper, synthetic paper and polyethylene-laminated paper; fabrics; glass fibers; and laminated composites of a plurality of the aforesaid materials.

To improve adhesion between the substrate and the adhesive layer, the substrate may be treated by primer coating, corona treatment, etching and plasma treatment.

To apply the composition, any known means or method for application may be used, for example, a comma coater, a lip coater, a roll coater, a die coater, a knife coater, a blade coater, a rod coater, a kiss-roll coater, and a gravure coater; screen printing, dipping and casting methods. The amount of the composition to be applied on a substrate may be such that a cured adhesive layer has a thickness of from 2 to 200 µm, particularly from 3 to 100 µm.

Curing conditions may be as follows, but not limited thereto: the peroxide-curable composition may be cured at 100 to 200 degrees C. for 30 seconds to 10 minutes; and the addition-reactive composition may be cured at 80 to 130 degrees C. for 30 seconds to 3 minutes.

The adhesive tape may be prepared by applying the composition on the substrate as described above, or by applying the composition on a release film or a release paper coated with a releasing agent, curing the composition and put the cured composition on the releasing film or paper on the aforesaid substrate to thereby transfer the cured layer to the substrate.

Articles to be masked by the present silicone adhesive tape made of the present adhesive composition are, for example, metals such as stainless steel, copper, iron; plated or antirust-treated metals as described above; glass; porcelain and pottery; ceramics; resins such as polytetrafluoroethylene, polyimide, epoxy resins and novolak resins; and composites thereof.

The present silicone adhesive composition gives an adhesive tape which can be peeled off without leaving adhesive residue after it is applied on a metal substrate, particularly stainless steel, to mask the substrate and heat-aged at 280 degrees C.

EXAMPLES

The present invention will be explained with reference to the following non-limiting Examples and Comparative Examples. The terms "parts" means parts by weight, "Me" means a methyl group, "Ph" means a phenyl group, "Bu" means a butyl group, and "Vi" means a vinyl group.

The following test methods were used.

Adhesive Residue

An adhesive tape was prepared by applying a solution of silicone adhesive composition on a polyimide film of 25 µm thickness and 25 mm width with an applicator in such a thickness that a thickness after cured was 40 µm. Then, the adhesive tape was cured at 165 degrees C. for 2 minutes after drying of f the solvent when the applied composition was a peroxide curable silicone adhesive, or at 130 degrees C. for 1 minute when the applied composition was an addition reactive silicone adhesive. The tape was attached on a polished stainless steel plate and pressed onto the metal plate by rolling a rubber-lined roller of 2 kg in weight back and forth in one cycle on the tape. Then, the metal plate with the tape thereon was left in a dryer at 280 degrees C. After a predetermined period of time, the metal plate with the tape thereon was taken out and cooled to room temperature. Then, the tape was peeled from the metal plate and observed whether any adhesive residues was left on the metal surface, due to the breakage of the adhesive layer. The tape was rated according to the following criteria.

No adhesive residue left: +

Adhesive residue left on a part of the plate surface: −

Adhesive residue left on the whole plate surface: −−

Adhesion Strength

An adhesive tape prepared as in the adhesive residue test was attached to a stainless steel plate and pressed onto the metal plate by rolling a rubber-lined roller of 2 kg in weight back and forth in one cycle on the tape. After leaving the metal plate with the tape thereon at room temperature for about 20 hours, a force in N/25 mm required to peel the tape off from the metal plate was measured using a tensile tester.

Holding Power

An adhesive tape was prepared as in the adhesive residue test. According to Japanese Industrial Standards Z0237-2000, the tape of about 75 mm in length was attached in an area of 25 by 25 mm on a lower end of a vertically held stainless steel plate. At the lower end of the tape, a weight of 1 kg was hung. After leaving the plate at 250 degrees C. for 1 hour, a displacement of the position of the upper end of the tape before and after this 1 hour was measured with a microscope.

Tack

An adhesive tape was prepared as in the adhesive residue test. Tack of the adhesive layer was measured with a Polyken probe tack tester, ex Testing Machines Inc., at a probe rate of 1.0 cm/s for a dwell time of 1.0 sec with a ring weight of 20 g.

Example 1

A solution was refluxed for 4 hours by heating which solution consisted of 45 parts of a phenyl group-containing polydimethylsiloxane which was end-capped with OH groups and had 6 mole % of diphenylsiloxane unit and a viscosity in a 30% solution in toluene of 42,000 mPa·s, 92 parts of a 60% solution in toluene of a polysiloxane having $Me_3SiO_{0.5}$ units and $SiO_2$ units with a ratio of $Me_3SiO_{0.5}$ unit/$SiO_2$ unit being 0.80 and a number average molecular weight of 2720, and 30 parts of toluene. After leaving the solution to cool, 0.2 part of a hindered amine compound I of the following formula, Adekastab LA57, ex Asahi Denka Co, Ltd., was added to the solution and mixed.

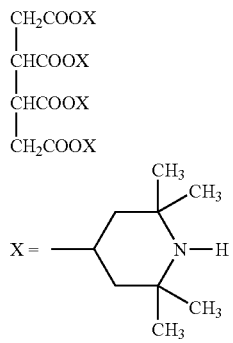

(I)

To 100 parts of the above mixture containing about 60% of siloxane, 2.4 parts of a 50% paste of benzoylperoxide in a silicone, and 50 parts of toluene were added to prepare a silicone adhesive composition solution containing about 40% of siloxane. The silicone adhesive was tested for adhesive residue, adhesion strength and holding power. The results are as seen in Table 1.

Example 2

Example 1 was repeated except that, instead of the hindered amine compound I, 0.2 part of a hindered amine compound II, Adekastab LA52, ex Asahi Denka Co, Ltd., represented by the following formula was used to prepare an adhesive composition solution.

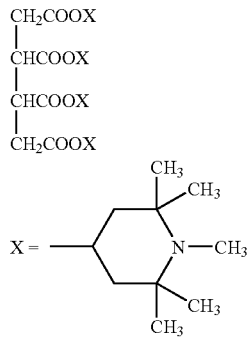

(II)

The silicone adhesive composition was tested for adhesive residue, adhesion strength and holding power. The results are as seen in Table 1.

Example 3

Example 1 was repeated except that 45 parts of a polydimethylsiloxane which was end-capped with OH groups and had a viscosity in a 30% solution in toluene of 67,000 mPa·s was used instead of the phenyl group-containing dimethylpolysiloxane to prepare an adhesive composition solution. The silicone adhesive composition was tested for adhesive residue, adhesion strength and holding power. The results are as seen in Table 1.

Comparative Example 1

A silicone adhesive composition solution was prepared without the hindered amine compound I. The silicone adhesive composition was tested for adhesive residue, adhesion strength and holding power. The results are as seen in Table 1.

Comparative Example 2

Example 1 was repeated except that, instead of the hindered amine compound I, use was made of a 0.5 part by weight of phenolic antioxidant III, IRGANOX 1330, ex Chiba Specialty Chemicals Co., represented by the following formula.

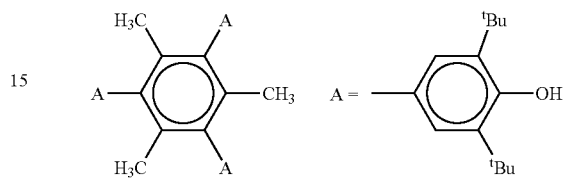

The silicone adhesive composition was tested for adhesive residue, adhesion strength and holding power. The results are as seen in Table 1.

Example 4

To a solution consisting of 45 parts of a polydimethylsiloxane containing vinyl and phenyl groups, which was end-capped with $SiMe_2Vi$ groups and has 0.15 mole % of methylvinylsiloxane unit and 10 mole % of diphenylsiloxane unit and a viscosity in a 30% solution in toluene of 27,000 mPa·s, 92 parts of a 60% solution in toluene of a polysiloxane comprising $Me_3SiO_{0.5}$ unit and $SiO_2$ unit with a ratio of $Me_3SiO_{0.5}$ unit/$SiO_2$ unit being 0.80, and 30 parts of toluene, were added and mixed 0.2 part of the hindered amine compound I, 0.16 part of a cross-linking agent of the following formula, and 0.1 part of ethynylcyclohexanol.

$Me_3SiO—[MeHSiO]_{40}—SiMe_3$

To 100 parts of the above mixture containing about 60% of siloxane, 50 parts of toluene and 0.5 part of a platinum catalyst, CAT-PL-50T, ex Shin-Etsu Chemical Co. Ltd., were added to prepare a silicone adhesive composition solution containing about 40% of siloxane. The silicone adhesive was tested for adhesive residue, adhesion strength and holding power. The results are as seen in Table 1.

Comparative Example 3

Example 4 was repeated except that, instead of the hindered amine compound I, 0.5 part of the aforesaid phenolic antioxidant III was used to prepare a silicone adhesive composition solution. The silicone adhesive was tested for adhesive residue, adhesion strength and holding power. The results are as seen in Table 1.

Example 5

To a solution consisting of 45 parts of polydimethylsiloxane containing vinyl and phenyl groups, which was end-capped with $SiMe_2Vi$ groups and had 0.15 mole % of methylvinylsiloxane unit and 10 mole % of diphenylsiloxane unit and a viscosity in a 30% solution in toluene of 27,000 mPa·s, 92 parts of a 60% solution in toluene of a polysiloxane comprising $Me_3SiO_{0.5}$ units and $SiO_2$ units with a ratio of $Me_3SiO_{0.5}$ unit/$SiO_2$ unit being 0.80, and 30 parts of toluene, were added and mixed 0.2 part of hindered amine compound I, 0.5 part of phenolic antioxidant III, 0.16 part of a crosslinking agent of the following formula, and 0.1 part of ethynylcyclohexanol.

Me$_3$SiO—[MeHSiO]$_{40}$—SiMe$_3$

To 100 parts of the above mixture containing about 60% of siloxane, 50 parts of toluene and 0.5 part of a platinum catalyst, CAT-PL-50T, ex Shin-Etsu Chemical Co. Ltd., were added to prepare a silicone adhesive composition solution containing about 40% of siloxane. The silicone adhesive was tested for adhesive residue, adhesion strength and holding power. The results are as seen in Table 1.

Example 6

Example 4 was repeated except that 0.2 part of the hindered amine compound IV of the following formula, Adekastab 77Y, ex Asahi Denka Co, Ltd.,

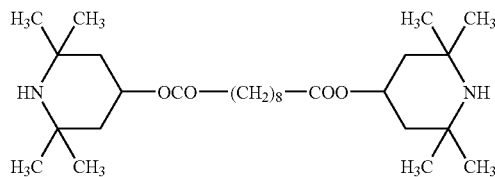

was used instead of the hindered amine compound I to prepare a silicone adhesive composition solution. The silicone adhesive was tested for adhesive residue, adhesion strength and holding power. The results are as seen in Table 1.

Example 7

A solution was refluxed for 4 hours by heating which solution consisted of 40 parts of a polydimethylsiloxane which was end-capped with OH groups and had a viscosity in a 30% solution in toluene of 67,000 mPa·s, 100 parts of a 60% solution in toluene of a polysiloxane having Me$_3$SiO$_{0.5}$ units and SiO$_2$ units with a ratio of Me$_3$SiO$_{0.5}$ unit/SiO$_2$ unit being 0.80 and a number average molecular weight of 2720, and 27 parts of toluene. After leaving the solution to cool, 0.2 part of the hindered amine compound IV of the above formula was added to the solution and mixed.

To 100 parts of the obtained mixture containing about 60% of siloxane, 2.4 parts of a 50% paste of benzoylperoxide in a silicone, and 50 parts of toluene were added to prepare a silicone adhesive composition solution containing about 40% of siloxane. The silicone adhesive was tested for adhesive residue, adhesion strength and holding power. The results are as seen in Table 1.

Example 8

A solution was refluxed for 4 hours by heating which solution consisted of 40 parts of a phenyl group-containing polydimethylsiloxane which was end-capped with OH groups and had 6 mole % of diphenylsiloxane unit and a viscosity in a 30% solution in toluene of 42,000 mPa·s, 100 parts of a 60% solution in toluene of a polysiloxane having Me$_3$SiO$_{0.5}$ units and SiO$_2$ units with a ratio of Me$_3$SiO$_{0.5}$ unit/SiO$_2$ unit being 0.77 and a number average molecular weight of 2550, and 27 parts of toluene. After leaving the solution to cool, 0.15 part of the hindered amine compound I was added to the solution and mixed. To 100 parts of the obtained mixture containing about 60% of siloxane, 2.4 parts of a 50% paste of benzoylperoxide in a silicone, and 50 parts of toluene were added to prepare a silicone adhesive composition solution containing about 40% of siloxane. The silicone adhesive was tested for adhesive residue, adhesion strength and holding power. The results are as seen in Table 1.

Example 9

A solution was refluxed for 4 hours by heating which solution consisted of 41 parts of a phenyl group-containing polydimethylsiloxane which was end-capped with OH groups and had a viscosity in a 30% solution in toluene of 67,000 mPa·s, 98.3 parts of a 60% solution in toluene of a polysiloxane having Me$_3$SiO$_{0.5}$ units and SiO$_2$ units with a ratio of Me$_3$SiO$_{0.5}$ unit/SiO$_2$ unit being 0.84 and a number average molecular weight of 1900, and 27.4 parts of toluene. After leaving the solution to cool, 0.20 part of the hindered amine compound II was added to the solution and mixed. To 100 parts of the obtained mixture containing about 60% of siloxane, 2.4 parts of a 50% paste of benzoylperoxide in a silicone, and 50 parts of toluene were added to prepare a silicone adhesive composition solution containing about 40% of siloxane. The silicone adhesive was tested for adhesive residue, adhesion strength and holding power. The results are as seen in Table 1.

Comparative Example 4

Example 2 was repeated except that a 60% solution in toluene of a polysiloxane having Me$_3$SiO$_{0.5}$ units and SiO$_2$ units with a ratio of Me$_3$SiO$_{0.5}$ unit/SiO$_2$ unit being 1.30 and a number average molecular weight of 1490 was used in place of the 60% solution in toluene of polysiloxane having a ratio of Me$_3$SiO$_{0.5}$ unit/SiO$_2$ unit of 0.80 and a number average molecular weight of 2720. The silicone adhesive composition obtained was tested in the same manner as in Example 2 and the results are shown in Table 1.

Comparative Example 5

Example 2 was repeated except that a 60% solution in toluene of a polysiloxane having Me$_3$SiO$_{0.5}$ units and SiO$_2$ units with a ratio of Me$_3$SiO$_{0.5}$ unit/SiO$_2$ unit being 1.10 and a number average molecular weight of 1570 was used in place of the 60% solution in toluene of polysiloxane having a ratio of Me$_3$SiO$_{0.5}$ unit/SiO$_2$ unit of 0.80 and a number average molecular weight of 2720. The silicone adhesive composition obtained was tested in the same manner as in Example 2 and the results are shown in Table 1.

Example 10

A solution was refluxed for 4 hours by heating which solution consisted of 40 parts of a vinyl group-containing polydimethylsiloxane which was end-capped with dimethylvinylsilyl groups and had 0.05 mole % of methylvinyl siloxane unit and a viscosity in a 30% solution in toluene of 43,000 mPa·s, 100 parts of a 60% solution in toluene of a polysiloxane having Me$_3$SiO$_{0.5}$ units and SiO$_2$ units with a ratio of Me$_3$SiO$_{0.5}$ unit/SiO$_2$ unit being 0.85 and a number average molecular weight of 3210, and 27 parts of toluene. After leaving the solution to cool, 0.4 part of the hindered amine compound II, 0.26 part of a cross-linking agent of the following formula, and 0.1 part of ethynylcyclohexanol.

Me$_3$SiO—[MeHSiO]$_{40}$—SiMe$_3$

To 100 parts of the above mixture containing about 60% of siloxane, 50 parts of toluene and 0.5 part of a platinum catalyst, CAT-PL-50T, ex Shin-Etsu Chemical Co. Ltd., were added to prepare a silicone adhesive composition solution containing about 40% of siloxane. The silicone adhesive was tested for adhesive residue, adhesion strength and holding power. The results are as seen in Table 2.

Example 11

Example 10 was repeated except that 0.6 part of the hindered amine compound II was added. The silicone adhesive composition obtained was tested in the same manner as in Example 10 and the results are shown in Table 2.

Example 12

Example 10 was repeated except that 1.0 part of the hindered amine compound II was added. The silicone adhesive composition obtained was tested in the same manner as in Example 10 and the results are shown in Table 2.

Comparative Example 6

Example 10 was repeated except that the hindered amine compound II was not added. The silicone adhesive composition obtained was tested in the same manner as in Example 10 and the results are shown in Table 2.

What is claimed is:

1. An addition-reactive silicon adhesive composition comprising:

20 to 80 parts by weight of a diorganopolysiloxane (A'), having 2 or more alkenyl groups which has 2 or more alkenyl groups and is represented by any one of the following formulae

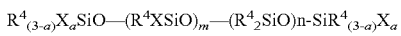

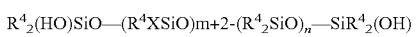

where $R^4$ is a monovalent hydrocarbon group free of an aliphatic unsaturated bond, X is an organic group having an alkenyl group, a is an integer of from 0 to 3, m is at least 0, provided that a and m being not zero at the same time, n is at least 100, and m+n is such a number that a viscosity of the diorganopolysiloxane at 25 degrees C is 500 mPa·s or higher, 80 to 20 parts by weight of a polyorganosiloxane (B) comprising $R^1_3SiO_{0.5}$ unit and $SiO_2$ unit in a molar ratio of the $R^1_3SiO_{0.5}$ unit to the $SiO_2$ unit of from 0.6 to 1.0, wherein $R^1$ is a monovalent hydrocarbon group having 1 to 10 carbon atoms, 0.01 to 1.0 part by weight, based on a total of (A') and (B) of 100 parts by weight, of a hindered amine compound (C) having the moiety represented by the following formula,

TABLE 1

|  | Additive(s), part by weight | Adhesive residue vs. aging time, min | | | | | | Adhesion strength, N/25 mm | Holding power, mm |
| --- | --- | --- | --- | --- | --- | --- | --- | --- | --- |
|  |  | 30 | 60 | 90 | 120 | 150 | 180 |  |  |
| Example 1 | I, 0.2 | + | + | + | + | + | + | 5.5 | 0.5 |
| Example 2 | II, 0.2 | + | + | + | + | + | − | 5.3 | 0.6 |
| Example 3 | I, 0.2 | + | + | + | + | − | − | 4.7 | 0.5 |
| Example 4 | I, 0.2 | + | + | + | + | − | − | 5.2 | 0.06 |
| Example 5 | I, 0.2 III, 0.5 | + | + | + | + | + | + | 5.1 | 0.07 |
| Example 6 | IV, 0.2 | + | + | + | − | − | − | 5.9 | 0.02 |
| Example 7 | IV, 0.2 | + | + | + | + | − | − | 7.3 | 1.51 |
| Example 8 | I, 0.15 | + | + | + | + | + | + | 8.2 | 0.48 |
| Example 9 | II, 0.2 | + | + | + | + | − | − | 6.3 | 0.63 |
| Comparative Example 1 | None | − | -- | -- | -- | -- | -- | 5.2 | dropped |
| Comparative Example 2 | III, 0.5 | + | − | -- | -- | -- | -- | 5.2 | dropped |
| Comparative Example 3 | III, 0.2 | + | − | -- | -- | -- | -- | 4.8 | 0.08 |
| Comparative Example 4 | II, 0.2 | -- | -- | -- | -- | -- | -- | 1.4 | dropped |
| Comparative Example 5 | II, 0.2 | -- | -- | -- | -- | -- | -- | 2.3 | dropped |

TABLE 2

|  | Additive(s), part by weight | Adhesive residue vs. aging time, min | | | | Adhesion strength, N/25 mm | Holding power, mm | Tack, gf |
| --- | --- | --- | --- | --- | --- | --- | --- | --- |
|  |  | 30 | 60 | 120 | 180 |  |  |  |
| Example 10 | II, 0.4 | + | + | + | − | 8.3 | 0.01 | 700 |
| Example 11 | II, 0.6 | + | + | + | − | 8.6 | 0.01 | 470 |
| Example 12 | II, 1.0 | + | + | + | − | 8.7 | 0.01 | 245 |
| Comparative Example 6 | None | -- | -- | -- | -- | 8.2 | 0.02 | 810 |

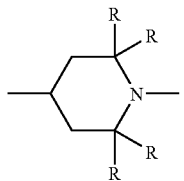

wherein R is a monovalent hydrocarbon group having 1 to 6 carbon atoms,
a polyorganosiloxane (E) having SiH group in such an amount that a molar ratio of the SiH group to the alkenyl group of the component (A') ranges from 0.5 to 20,
0 to 8.0 part by weight, based on a total of (A') and (B) of 100 parts by weight, of a retarder (F), and
a platinum catalyst (G) in such an amount that an amount as platinum ranges from 1 to 5000 ppm based on a total of (A') and (B) of 100 parts by weight.

2. The addition-reactive silicon adhesive composition according to claim 1, wherein the diorganopolysiloxane (A') comprises 1 to 35 mole % of diphenylsiloxy unit.

3. The addition-reactive silicon adhesive composition according to claim 1, wherein the composition further comprises 0.1 to 10 parts by weight, based on a total of (A') and (B) of 100 parts by weight, of a phenolicantioxidant (H).

4. The addition-reactive silicon adhesive composition according to claim 1, wherein the polyorganosiloxane (B) has a molar ratio of the $R^1{}_3SiO_{0.5}$ unit to the $SiO_2$ unit in the range of from 0.7 to 0.9.

5. The addition-reactive silicon adhesive composition according to claim 1, wherein hindered amine compound (C) is selected from the group consisting of the following compounds:

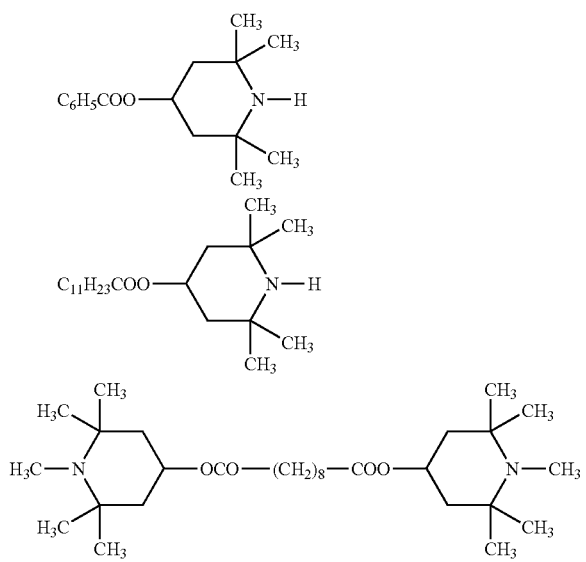

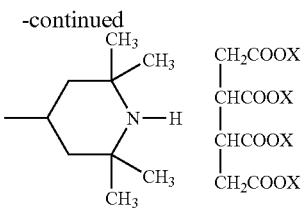

-continued

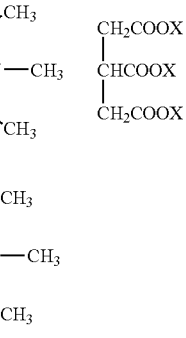

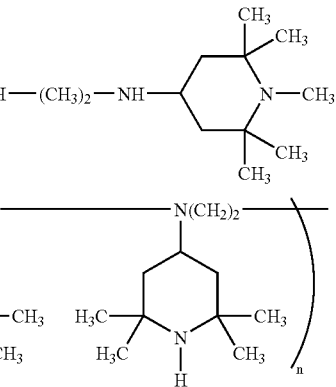

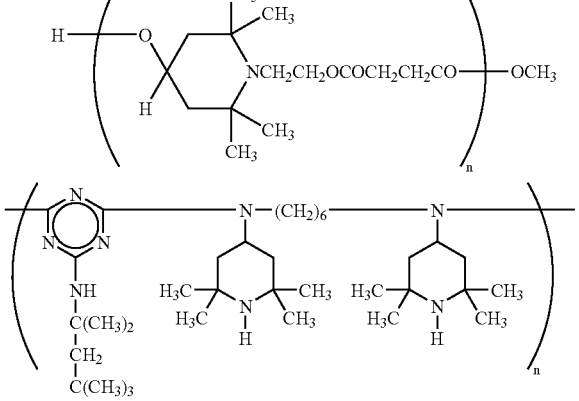

wherein n is an integer of from 2 to 20.

6. An adhesive tape comprising a plastic film and an adhesive applied on at least one side of the plastic film, the adhesive being made by curing the adhesive composition according to claim 1.

* * * * *